US008000512B2

(12) United States Patent
Sabol et al.

(10) Patent No.: US 8,000,512 B2
(45) Date of Patent: Aug. 16, 2011

(54) SLIT COLLIMATOR SCATTER CORRECTION

(75) Inventors: John Michael Sabol, Sussex, WI (US); Kadri Nizar Jabri, Waukesha, WI (US); Adam Ellis Boden, Waukesha, WI (US); Meghan Lynn Yue, Johnson Creek, WI (US)

(73) Assignee: General Electric Company, Niskayuna, NY (US)

( * ) Notice: Subject to any disclaimer, the term of this patent is extended or adjusted under 35 U.S.C. 154(b) by 986 days.

(21) Appl. No.: 11/866,878

(22) Filed: Oct. 3, 2007

(65) Prior Publication Data

US 2009/0092307 A1 Apr. 9, 2009

(51) Int. Cl.
*G06K 9/00* (2006.01)
*H05G 1/64* (2006.01)
(52) U.S. Cl. .................. 382/132; 382/274; 378/98.9
(58) Field of Classification Search .................. 382/100, 382/128, 129, 130, 131, 132, 133, 134, 168, 382/173, 181, 232, 254, 274, 276, 295, 305, 382/312; 250/582; 378/98.9, 54, 98.3, 62
See application file for complete search history.

(56) References Cited

U.S. PATENT DOCUMENTS

| 6,031,892 | A * | 2/2000 | Karellas | 378/98.3 |
|---|---|---|---|---|
| 6,411,729 | B1 * | 6/2002 | Grunkin | 382/132 |
| 6,490,339 | B2 * | 12/2002 | Mitchell et al. | 378/62 |
| 6,717,174 | B2 * | 4/2004 | Karellas | 250/582 |
| 7,203,274 | B2 * | 4/2007 | Charles et al. | 378/54 |
| 7,724,875 | B2 * | 5/2010 | Jabri et al. | 378/98.9 |
| 2004/0120457 | A1 * | 6/2004 | Karellas et al. | 378/62 |

OTHER PUBLICATIONS http://en.wikipedia.org/wiki/Osteoporosis.
Robert A. Kruger, Dual-Energy Electronic Scanning-Slit Fluorography for the Determination of Vertebral Bone Mineral Content, Medical Physics, Jul./Aug. 1987, pp. 562-566, vol. 14, Issue 4, 1987 American Association of Physicists in Medicine.
P. J. Ryan, Overview of Role of BMD Measurements in Managing Osteoporosis, Seminars in Nuclear Medicine, Jul. 1997, pp. 197-209, vol. XXVII, No. 3, 1997 W. B. Saunders Company.
Glen M. Blake et al., Technical Principles of Dual Energy X-Ray Absorptiometry, Seminars in Nuclear Medicine, Jul. 1997, pp. 210-228, vol. XXVII, No. 3, 1997 W. B. Saunders Company.

(Continued)

*Primary Examiner* — Seyed Azarian
(74) *Attorney, Agent, or Firm* — Fletcher Yoder (57) ABSTRACT

A technique is presented for establishing a patient's BMD using a dual-energy X-ray imaging system. In the technique, the dual-energy X-ray imaging system utilizes a slit collimator to expose a series of portions of a region of interest within a patient with X-rays of two different energies. A flat-panel digital X-ray detector detects the X-rays passing through the patient's region of interest and produces data representative of the intensity of the X-rays reaching the detector. The image intensity data is corrected for scatter based on identifying the regions of the image intensity data that are produced from scatter only, and not primary X-rays. A first-order derivative of the image intensity data is used to identify these regions. A value for the intensity of the scatter at the boundary of the scatter-only region is established. The value for the intensity of the scatter at the boundary of the scatter-only region is used to estimate scatter intensity in the region of the image intensity data that is produced from primary X-rays, as well as scatter. To correct the image intensity data for scatter, the known and estimated scatter intensities are subtracted from the image intensity data.

24 Claims, 7 Drawing Sheets

OTHER PUBLICATIONS

S. K. Ahn et al., A Scatter Correction Using Thickness Iteration in Dual-Energy Radiography, IEEE Transactions on Nuclear Science, Feb. 2006, pp. 133-138, vol. 53, No. 1, 2006 IEEE.

Xingming Liu et al., Rejection and Redistribution of Scattered Radiation in Scan Equalization Digital Radiography (SEDR): Simulation with Spot Images, Medical Physics, Jul. 2007, pp. 2718-2729, vol. 34, Issue 7, 2007 American Association of Physicists in Medicine.

Boyer et al., Basic Applications of Multileaf Collimators, American Association of Physicists in Medicine, AAPM Report No. 72, Jul. 31, 2001.

* cited by examiner

— SCATTER CORRECTED
— ORIGINAL
---- ESTIMATED SCATTER

FIG. 10

— SCATTER CORRECTED
— ORIGINAL
---- ESTIMATED SCATTER

——SCATTER CORRECTED
—— ORIGINAL
---- ESTIMATED SCATTER

FIG. 13

——SCATTER CORRECTED
—— ORIGINAL
---- ESTIMATED SCATTER

SLIT COLLIMATOR SCATTER CORRECTION

BACKGROUND

The invention relates generally to medical imaging. In particular, the invention relates to digital X-ray medical imaging systems having a flat-panel digital X-ray detector.

The bone mineral density (BMD) of a bone reflects the strength of the bone as represented by calcium content. It is defined as the integral mass of bone mineral per unit of projected area in grams per square centimeter. BMD is a useful tool for the diagnosis and treatment of several diseases and conditions, one of which is osteoporosis.

Osteoporosis is a disease of bone in which the BMD is reduced due to depletion of calcium and bone protein. Osteoporosis predisposes a person to fractures, which are often slow to heal and heal poorly. It is more common in older adults, particularly post-menopausal women; in patients on steroids; and in those who take steroidal drugs. Unchecked osteoporosis can lead to changes in posture, physical abnormality (particularly a condition known colloquially as "dowager's hump"), and decreased mobility. Treatment of osteoporosis includes ensuring that the patient's diet contains adequate calcium and other minerals needed to promote new bone growth, and for post-menopausal women, estrogen or combination hormone supplements.

Dual-energy X-ray absorptiometry (DXA or DEXA) is an increasingly important bone density measurement technology. In fact, osteoporosis is defined by the World Health Organization (WHO) as a BMD having a value 2.5 standard deviations below peak bone mass (in a 20-year-old sex-matched healthy person average) as measured by DXA. The fundamental principle behind DXA is the measurement of the transmission of X-rays with two different energy levels. By measuring how much X-ray energy is transmitted through the patient, the amount of X-ray energy that is absorbed in the patient can be determined. Soft tissues and bone absorb the two energy level X-rays to different degrees. As a result, the absorption of X-rays by the soft tissue may be distinguished from the absorption of X-rays by bone. The BMD is then determined from the bone image data.

Because of the limitations in the size of early digital X-ray detectors, techniques were developed to perform DXA by moving the detector in conjunction with an X-ray source to cover the desired region of interest, such as the hip or vertebra. Examples of this type of DXA are pencil beam DXA and fan beam DXA. In pencil beam DXA, the X-ray source and detector perform a two-dimensional raster scan of the region of interest. In fan beam DXA, a slit collimator is used to produce a fan-shaped beam that extends across the region of interest such that the region of interest may be covered with a single sweep of the source and detector.

When X-rays interact with tissues and bone in a patient, some of the X-rays are deflected or redirected. These redirected X-rays are known as scatter. Scatter can produce a significant level of error in the quantitative values obtained during DXA. Other than having a different direction or energy, scattered X-rays are indistinguishable from the primary X-rays coming directly from the source and are included in the image used to derive the BMD. Thus, the intensity of X-rays that would appear to have been transmitted through the soft tissue and bone may be greater than the actual amount of radiation received at pixel locations of a detector due to the detection of scattered radiation. Conversely, the intensity of X-rays that would appear to have been transmitted through the soft tissue and bone would appear to be less than the actual amount that would have received the X-rays if not for scatter. In addition to affecting the clarity of the image, the values for the BMD would also be affected by scatter.

Existing DXA systems have narrow collimation and a small field of view which enables these systems to minimize the effects of scatter. However, digital X-ray detector technology has now advanced to the point where large flat-panel digital X-ray detectors are large enough to cover significantly-sized regions of clinical interest. As a result, the digital X-ray detector may remain stationary relative to the patient. In addition, the effect of scatter is much greater than in existing DXA systems. Techniques to reduce scatter during acquisition, such as anti-scatter grids and air gaps, may be used to reduce scatter. However, these techniques attenuate the X-rays and do not completely remove the effect of scatter. As a result, the patient must be exposed to greater amounts of X-rays to achieve the desired results.

Therefore, a technique is desired that would reduce the effects of scatter when a large, flat-panel digital detector is used. In particular, a technique is desired that would reduce the effects of scatter, while reducing, or at least not increasing, a patient's exposure to X-rays.

BRIEF DESCRIPTION

A technique is presented for establishing a patient's BMD using a dual-energy X-ray imaging system. In the technique, the dual-energy X-ray imaging system utilizes a slit collimator to expose a series of portions of a region of interest within a patient with X-rays of two different energies. A flat-panel digital X-ray detector detects the X-rays passing through the patient's region of interest and produces data representative of the intensity of the X-rays reaching the detector. After correcting the image intensity data for scatter, the image intensity data for each portion of the patient's region of interest can be combined to form one or more images of the region of interest. The BMD is established from the scatter-corrected image intensity data, as well.

The scatter correction technique is based on identifying the regions of the image intensity data that reflect the detection of X-rays only from scatter, and not from any primary X-rays. A first-order derivative of the image intensity data is used to identify these regions. A value representative of the intensity of the scatter at the boundary of the scatter-only region is established. This value for the intensity of the scatter at the boundary of the scatter-only region is used to estimate scatter intensity in the region of the image intensity data that is produced from both primary X-rays and scatter. In one embodiment of the technique, the value for the intensity of the scatter at the boundary of the scatter-only region is multiplied by a scatter correction factor to estimate the scatter intensity in the center of the region of the image intensity data that is produced from primary X-rays, as well as scatter. The scatter in the remaining portion of this region is interpolated using the estimated intensity at a point within the region. To correct the image intensity data for scatter, the known and estimated scatter intensities are subtracted from the image intensity data.

DRAWINGS

These and other features, aspects, and advantages of the present invention will become better understood when the following detailed description is read with reference to the accompanying drawings in which like characters represent like parts throughout the drawings, wherein.

DETAILED DESCRIPTION

Figure 1:
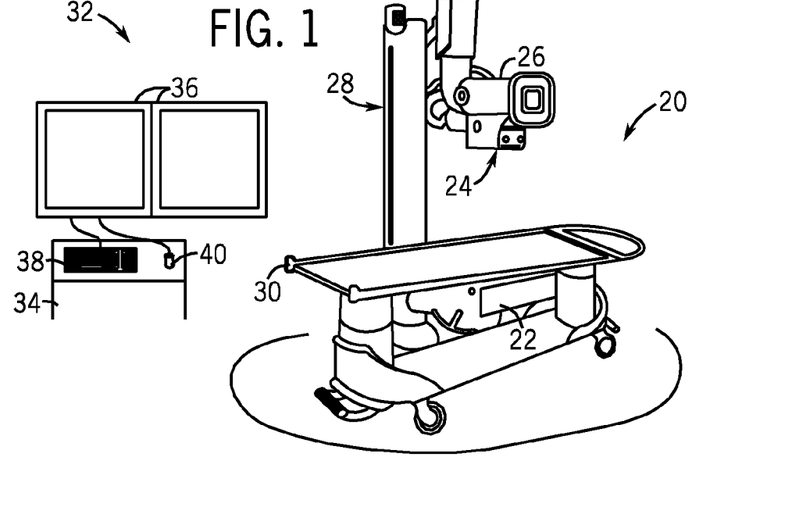
FIG. 1 is a schematic view of a dual-energy X-ray medical imaging system having a large, flat-panel digital X-ray detector and operable to perform dual-energy X-ray absorptiometry (DXA), in accordance with an exemplary embodiment of the present technique.

Referring now to FIG. 1, the present invention will be described as it might be applied in conjunction with an exemplary imaging system, in this case a dual-energy X-ray imaging system, as represented generally by reference numeral 20. In this embodiment, the dual-energy X-ray imaging system 20 is operable to perform dual-energy X-ray absorpiometry (DXA). In general, however, it should be borne in mind that the present techniques may be used with any suitable imaging modality. In particular, this technique is applicable for any imaging system using a large, flat-panel digital detector.

In the illustrated embodiment, the system 20 has a large, flat-panel digital X-ray detector 22, and a slit collimator 24 disposed over an X-ray source 26. The dual-energy X-ray imaging system 20 is capable of producing images of bone and soft tissue by taking images using X-rays of different energy. In particular, the system 20 is capable of producing an image of a region of interest using X-rays having a first energy level and then producing an image of a region of interest using X-rays having a second energy level. In this embodiment, the X-rays produced at the first energy level are lower in energy than the X-rays produced at the second energy level. The two images may be combined digitally, or analyzed to distinguish tissues, evaluate qualities of tissues, and so forth. Soft tissues and bone absorb the lower energy X-rays and the higher energy X-rays to different degrees, enabling the system 20 to distinguish the absorption and attenuation of X-rays by soft tissue and the absorption and attenuation by bone.

In the illustrated embodiment, the flat-panel digital X-ray detector 22 is an amorphous silicon flat panel that has the ability to acquire two images in rapid succession. This image acquisition speed enables high and low energy images with large energy separation (up to 90 kVp) translating to improved image subtraction. In this embodiment, the detector 22 and X-ray source 26 of the dual-energy X-ray imaging system 20 are mounted on a tilting wall stand 28. As will be discussed in more detail below, instead of exposing the entire surface area of the detector 22 at once, the slit collimator 24 is used to take an image strip using a smaller portion of the detector 22. The tilting wall stand 28 is adapted to pivot the X-ray source 26 and slit collimator 24 to enable the system to take a series of image strips that then could be combined together digitally to form a larger image. The system 20 also utilizes a mobile stretcher or table 30 upon which patients may lie during imaging procedures. Alternatively, the system may be configured with the flat-panel digital X-ray detector 22 and X-ray source 26 secured to different supports. For example, the flat-panel digital X-ray detector 22 may be secured to a stand that enables the detector 22 to be oriented vertically, while the X-ray source 26 is suspended from the ceiling using a separate support. In addition, the illustrated embodiment of the system 20 has an operator station 32 that uses a computer 34 to control the system 20 and to process the images. The operator's station 32 includes two monitors 36, a keyboard 38, and a mouse 40 in this embodiment (or other interface components) to facilitate interactions between the system 20 and a user.

Figure 2:
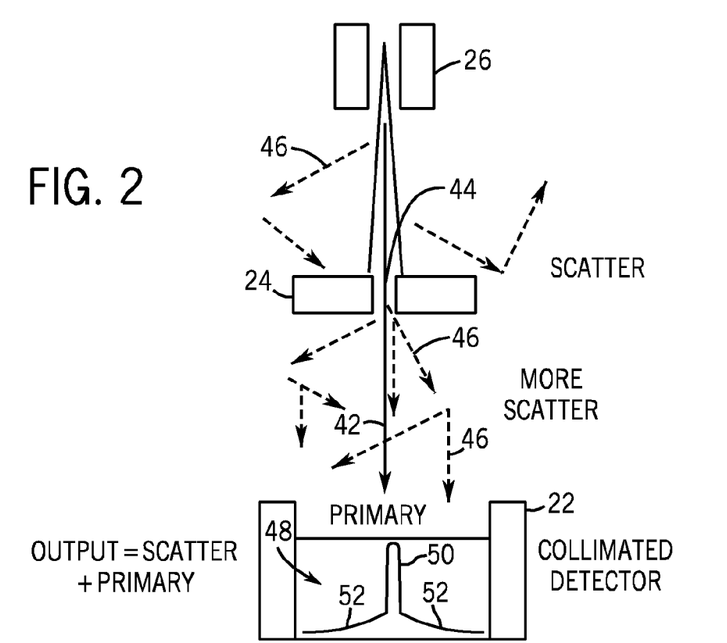
FIG. 2 is a diagrammatical representation of the X-ray source, slit collimator, and large, flat-panel digital X-ray detector of FIG. 1, in accordance with an exemplary embodiment of the present technique.

Referring generally to FIG. 2, the slit collimator 24 is used to produce a more accurate image of the patient by filtering stray X-rays from the patient and detector 22. Ideally, the only X-rays that strike the detector 22 are X-rays that have traveled from the X-ray source 26, through a patient, to the detector 22 in a direct path. The X-rays that travel in the desired path are known as "primary" X-rays 42. The primary X-rays 42 are able to pass through a slit 44 in the slit collimator 24. The slit collimator 24 blocks stray X-rays produced by the X-ray source 26 from striking the patient. However, other X-rays that are detected by the detector 22 do not follow this direct path. These X-rays are known as scatter 46. Primarily, scatter 46 is X-rays that have interacted with the tissues of the patient and been deflected or redirected off of their original path.

Scatter has the effect of skewing the results of the detection of absorption and attenuation of X-rays within the subject. The detector 22 has pixels that detect both primary X-rays 42 and scatter 46. To the pixel of the detector 22 that is in line with the original path of the X-ray, a scattered X-ray would appear to have been absorbed. On the other hand, to the pixel of the detector 22 that detects the scattered X-ray, the scattered X-ray would appear to have passed directly through the patient normally. In each case, the scatter has induced error into the image intensity data and, thus, the medical image. This error reduces contrast in the image, and may appear as fuzziness in the image, and may adversely affect analyses performed based upon the image data.

A representative plot of the image intensity data, referenced generally by reference numeral 48, detected by the detector 22 is presented graphically on the detector 22. As will be discussed in more detail below, the image intensity data 48 is of a test phantom composed of materials simulating tissue densities, such as via uniform thicknesses of aluminum and a resin. The aluminum represents bone and the resin represents soft tissue. The greatest intensity within the image intensity data 48 occurs in the region of the detector 22 that is directly opposite of the slit 44. This region, as represented generally by reference numeral 50, of the image intensity data 48 is due to the detection of both primary X-rays 42 and scatter X-rays 46 by the detector 22. The sloped intensities, referenced generally by reference numeral 52, in the image intensity data 48 represent the detection of scatter X-rays only. These "scatter-only" regions 52 of the image intensity data 48 do not represent the detection of any primary X-rays 42 because the slit collimator 24 blocks the primary X-rays 42 from reaching the corresponding portions of the detector 22.

As will be discussed in more detail below, the illustrated embodiment of the system 20 utilizes a scatter correction technique to reduce the effect of scatter on images formed by the system 20 by identifying the regions 52 of the image intensity data 48 that are the products of scatter 46 only and then using the intensity of the scatter in these regions to estimate the intensity of the scatter 46 within the region 50 of the image intensity data 48 that is the product of both primary X-rays 42 and scatter 46. Furthermore, the only region of the image intensity data 48 that is used to form an image is the region 50 of the image intensity data 48 that is the product of both primary X-rays 42 and scatter X-rays 46. In this embodiment of the technique, the image intensity data 48 is corrected by subtracting the scatter intensity from the image intensity data 48, leaving only the image intensity data 48 that is the product of primary X-rays 42.

Figure 3:
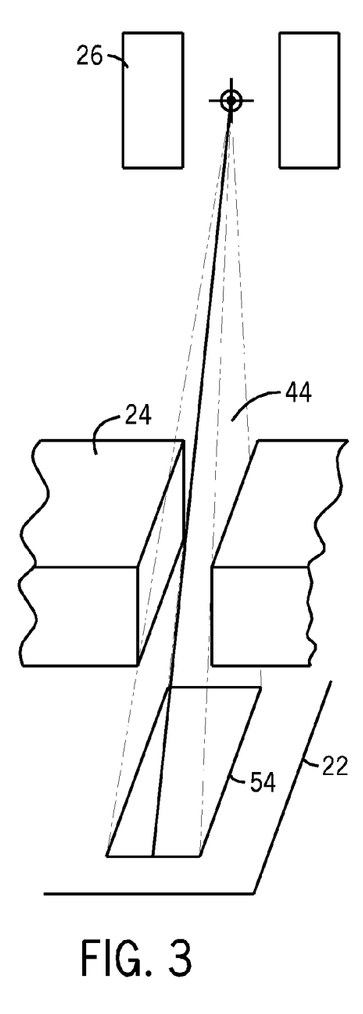
FIGS. 3 and 4 are three-dimensional views of the X-ray source and slit collimator of FIG. 2, in accordance with an exemplary embodiment of the present technique.
Figure 4:
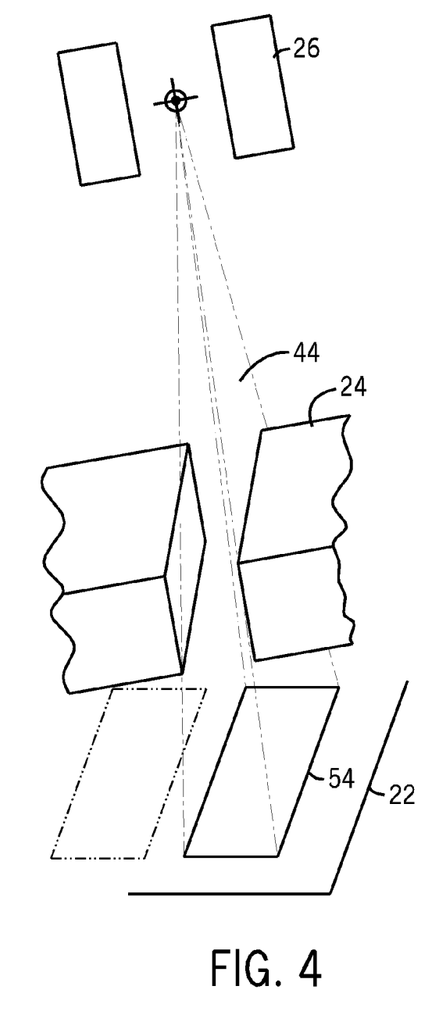

Referring generally to FIGS. 3 and 4, the X-ray source 26 and slit collimator 24 of the illustrated embodiment combine to form a rectangular image exposure area, reference generally by reference numeral 54. However, the X-ray source 26 and slit collimator 24 may be adapted to produce exposure areas having other shapes and sizes. In addition, in this embodiment of the system 20, the slit 44 is approximately 2.5 cm in width.

In this embodiment, the tilting wall stand 28 is adapted to pivot the X-ray source 26 and slit collimator 24 to move the rectangular exposure area 54 from a first position in FIG. 3 to a second position in FIG. 4. In this manner, the rectangular exposure area 54 is moved over the surface of the detector 22 so as to enable the system 20 to take a series of images that are combined digitally to form an image or images of the region of interest as a whole. There may be some overlap of portions of the detector 22 from one exposure to the next. In addition, the system may be configured to pivot to one position and then take both the higher and lower energy level images or the system 20 may go through a complete sequence of images with X-rays at one energy level and then repeat the sequence with X-rays at the other energy level.

Figure 5:
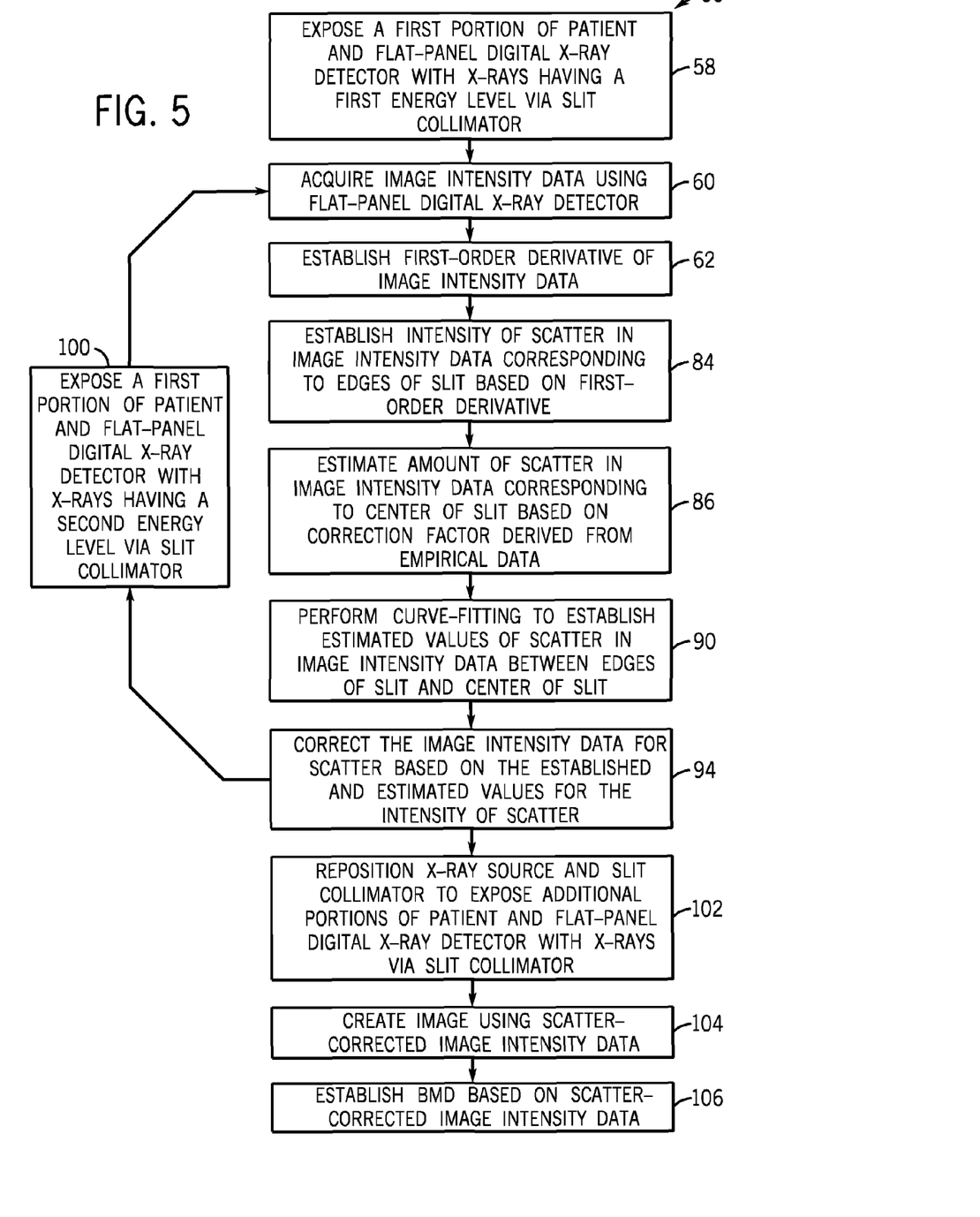
FIG. 5 is a block diagram of a process for establishing a patient's BMD using a dual-energy imaging system, in accordance with an exemplary embodiment of the present technique.

Referring generally to FIG. 5, a block diagram of a technique for establishing a patient's BMD using the dual-energy X-ray imaging system 20 is provided, and as represented generally by reference numeral 56. In this embodiment, the system 20 is used to expose a series of portions of the patient's region of interest with X-rays of two different energies to obtain image intensity data 48 for the region of interest that is, in turn, used to produce an image. After correcting the image intensity data for scatter, the images acquired from these exposures can then be combined to form one or more images of the region of interest. The BMD may then be determined by processing the corrected image data. The technique will now be discussed in more detail.

The slit collimator 24 and X-ray source 26 are used to expose a first portion of the patient and a corresponding portion of the flat-panel digital X-ray detector with X-rays having a first energy level, as represented generally by block 58. As described above, the slit collimator 24 collimates the X-ray beam produced by the system 20 to form a rectangular strip of X-rays. In this embodiment of the technique, the system 20 later uses X-rays of a second energy level to produce an image. In addition, in this embodiment, the first energy level is lower in energy than the second energy level.

The flat-panel digital detector 22 acquires the X-rays that pass through the patient and produces image intensity data representative of the intensity of X-rays detected by the detector 22, as represented generally by block 60. The system 20 then determines a first-order derivative of the image intensity data, as represented generally by block 62. The first-order derivative of the image intensity data enables the portions of the intensity image data that are due to the detection of scatter only to be identified.

Figure 6:
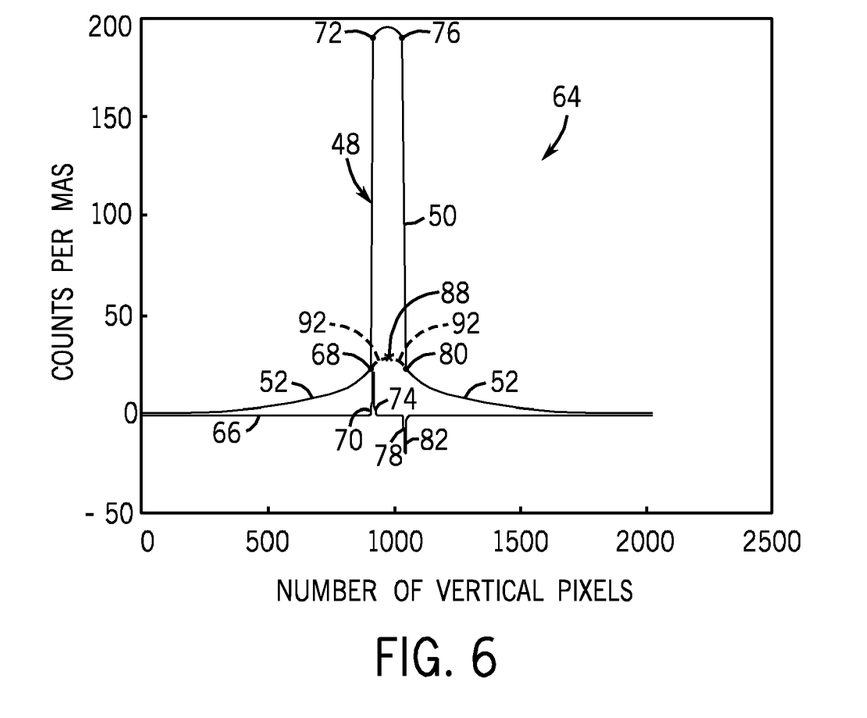
FIG. 6 is a plot of image intensity and the first-order derivative of the image intensity for an acquired image of a uniform sample simulating different tissue densities, in accordance with an exemplary embodiment of the present technique.

Referring generally to FIG. 6, a chart, as represented generally by reference numeral 64, of the representative plot of image intensity data 48 is presented along with a plot of the first-order derivative of the image intensity data 48, as represented generally by reference numeral 66. As noted above in regard to FIG. 2, in the illustrated embodiment, the subject of the representative plot of image intensity data is a series of uniform strips of aluminum and resin that represent bone and soft tissue, respectively.

In the illustrated embodiment, the scatter-only regions 52 of the image intensity data comprise two regions 52 of image intensity data that lie on either side of the region 50 of the image intensity data that is the result of primary X-rays 42 and scatter 46. As noted above, the region 50 of the image intensity data that is the result of primary X-rays 42 and scatter 46 is detected on the portion of the detector 22 that is directly opposite of the slit 44 in the slit collimator 24.

Unfortunately, there is no clear distinguishing mark that separates a scatter-only 52 region of the image intensity data 48 from the region 50 that is due both to primary X-rays 42 and scatter 46. However, an identifying characteristic of the scatter-only regions 52 of the image intensity data 48 is that the intensity of the image intensity data 48 in these regions rises slowly until we reach a point where the image intensity data 48 begins to reflect the detection of primary X-rays 42. Therefore, the first-order derivative 66 of the image intensity data 48 generally will not change substantially from one pixel to the next in the scatter-only regions 52 of the image intensity data 48. However, the amount of scatter will increase more rapidly as the region of the image intensity data 48 is approached that corresponds to an edge of the slit 44 because scatter 46 is concentrated opposite of the slit 44. That is because scatter X-rays 46 are more likely to be deflected at a slight angle rather than a great angle and the concentration of the primary X-rays 43 that produce the scatter are located there. Therefore, the first-order derivative will increase more rapidly as the edge of the slit 44 is approached. Eventually, some of the primary X-rays are able to pass through the edge of the slit 44 to be detected by the detector 22. At this point, the image intensity data 48 will increase markedly; producing a first inflection point 68 in the image intensity data 48, and the first-order derivative 66 will have an abrupt change. In this example, the abrupt change is an upward spike 70. However, the abrupt change need not be as marked as a spike to indicate the transition from a scatter-only region 52 of image intensity data 48 to a scatter and primary X-rays region 50.

An abrupt change in the first-order derivative 66 defines the boundary between the region 50 of the image intensity data 48 that is due to primary X-rays, as well as scatter 46, and the region 52 that is due to scatter only. For example, an abrupt change in the first-order derivative may be defined as a given ratio of the first-order derivative to the maximum value of the first-order derivative. Following this example, the point, or points, in the first-order derivative that have a value corresponding to the given ratio to the maximum value of the first-order derivative are then used to define the boundary between the region 50 of the image intensity data 48 that is due to primary X-rays and scatter 46 and the region 52 that is due to scatter only. In this embodiment, the first upward spike 70 in the first-order derivative 66 marks the end of the scatter-only region 52 of the image intensity data 48 on the left side of the image intensity data 48. This point in the image intensity data 48 corresponds to primary X-rays 42 passing along the inner edge of the slit 44. Similarly, moving slightly inward from the region corresponding to the inner edge of the slit 44, the detector 22 will eventually be fully exposed to primary X-rays 42. Still more slightly inward, the intensity of the image intensity data 48 will begin to increase less markedly. As a result, the rate of increase in the image intensity data 48 will slow; producing another inflection point 72 in the image intensity data 48, and the first-order derivative 66 of the image intensity data will have a downward spike 74. The opposite effect occurs on the inner edge of the slit 44 on the opposite side. The number of primary X-rays 42 will begin to decrease, producing another inflection point 76 in the image intensity data 48 and a negative downward spike 78 in the first-order derivative. Eventually, all primary X-rays 42 are blocked by the slit collimator 24 and the intensity of the image intensity data 48 will be due solely to scatter. The rate of change in the intensity will decrease and another inflection point 80 in the image intensity data 48 occurs. An upward spike 82 in the first-derivative also occurs as the rate of decrease in intensity declines markedly. This marks the beginning of the scatter-only region 52 on the right side of the image intensity data 48. Continuing to the right, the intensity of the image intensity data 48 is due only to scatter 46.

Referring again to FIG. 5, the intensity of the scatter 46 corresponding to the edge of the slit 44 is established based on the first-order derivative 66 of the image intensity data 48, as represented generally by reference numeral 84. As noted above, the first upward spike 70 and the second upward spike 82 define the boundaries of the scatter-only regions 52 of the image intensity data 48. They also define the boundaries of the region 50 of the image intensity data 48 due to primary X-rays 42, as well as scatter 46. In this embodiment particular, the intensities of the scatter 46 at the first upward spike 70 and the second upward spike 82 are averaged to establish the intensity of the scatter 46 corresponding to the edge of the slit 44. However, other methodologies of establishing the intensity of the scatter 46 corresponding to the edge of the slit 44 may be used. For example, only one of the scatter intensities at the first upward spike 70 and the second upward spike 82 may be used. In addition, if there is a marked difference in position between the starting point of the upward spike and the ending point of the upward spike, the intensity corresponding to the point adjacent to the scatter-only region 52 of the image intensity data 48 is used in this embodiment.

The intensity of scatter 46 in the center of the region 50 of the image intensity data 48 due to primary X-rays 42, as well as scatter 46, is estimated based on the intensity of the scatter 46 at the edge of the slit 44 and a scatter correction ratio derived from empirical data, as represented generally by block 86. The center of the region of the image intensity data 48 that is due to both primary X-rays 42 and scatter 46 corresponds to the region of the detector 22 that is directly opposite of the center of the slit 44. Specifically, in this embodiment, the estimated scatter corresponding to the center of the region 50 of the image intensity data 48 due to both primary X-rays 42 and scatter 46 is established by multiplying the scatter intensity at the edges of the slit 44 by the scatter correction ratio.

The ratio of the center scatter intensity to the edge scatter intensity was found by taking a series of slit images of uniform resin and aluminum test phantoms of differing thickness. In this embodiment, the scatter correction ratios are calculated by taking the average of the scatter ratios for a given range of aluminum and resin thicknesses. In addition, in this embodiment, two scatter correction ratios were established, one for each of the two X-ray energy levels used. During imaging, the scatter correction ratios may be selected based on the characteristics of the patient, such as weight, percent body fat, height, chest size, waist size, body mass index, the region of interest, etc. For example, a person with a greater percentage of body fat would have a greater percentage of soft tissue than bone, which could affect the amount of scatter being produced. Similarly, depending on the portion of the patient's body that is being imaged, more or less scatter may be expected. The patient's characteristic may be entered manually by an operator. Alternatively, the patient information may be retrieved automatically from an electronic record having the patient's characteristic stored within.

Referring again to FIG. 6, the estimated center scatter intensity 88 and the scatter at the two edges are the anchor points for modeling scatter in the region 50 of the image intensity data 48 that is due both to primary X-rays 42 and scatter 46. In the illustrated embodiment, scatter in the remaining portions of the region 50 is estimated by interpolation between these three points of the image intensity data 48. However, a technique other than interpolation may be used to estimate the intensity of the scatter 46 in the region 50 of the image intensity data 48 that is due both to primary X-rays 42 and scatter 46. In addition, points other than the center scatter intensity may be estimated. In addition, multiple points may be estimated.

Referring again to FIGS. 5 and 6, a curve-fitting program is used to interpolate scatter in the region 50 of the image intensity data 48 that is due both to primary X-rays 42 and scatter, as represented by block 90. The curve 92 joins the two scatter intensities at the two edges with the estimated scatter intensity at the center of the region 50 receiving X-rays due to primary X-rays and scatter. In the illustrated embodiment, a cubic-spline interpolation scheme is used to interpolate the scatter. However, another interpolation scheme may be used.

Figure 7:
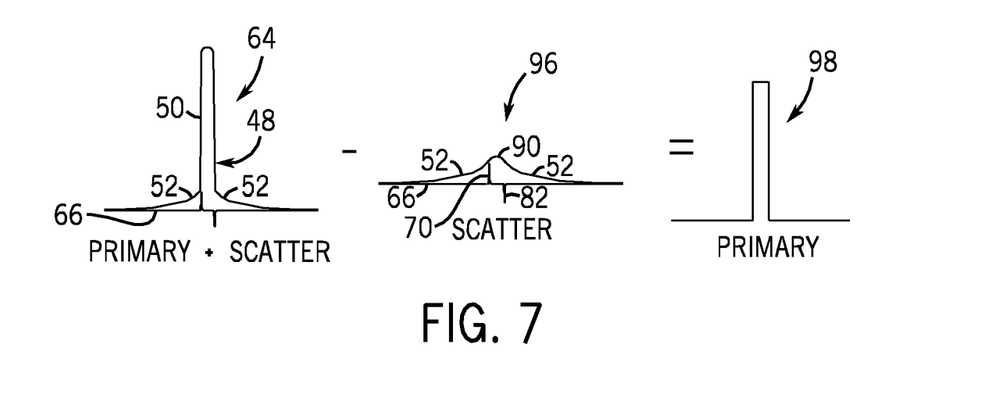
FIG. 7 is a graphical representation of the scatter-correction technique of FIG. 5 applied to the image intensity data of the sample of FIG. 6, in accordance with an exemplary embodiment of the present technique.

Referring generally to FIGS. 5 and 7, the image intensity data 48 is corrected for scatter based on the intensities of the scatter 46 in the scatter-only region 52 of the image intensity data 48 and the estimated intensities for scatter in the region 50 of the image intensity data 48 due both to primary X-rays 42 and scatter 46, as represented by block 94. In FIG. 7, the scatter correction technique is represented graphically. On the left are the original plots 64 of image intensity data 48 and the first-order derivative 66 of the image intensity data 48. In the center is a plot 96 of the scatter-only regions 52 of the original uncorrected image intensity data 48 and the curve 92 of estimated values for the intensity of the scatter 46 within the region of image intensity data 48 due to both primary X-rays 42 and scatter 46. To correct the image intensity data 48 for scatter, the scatter-only regions 52 of the original image intensity data 48 and the curve 92 of estimated values for the intensity of the scatter within the region 50 due both to primary X-rays 42 and scatter 46 are subtracted from the original uncorrected image intensity data 48. The resulting scatter corrected image intensity data, referenced generally by reference numeral 98, is displayed on the right. It should be noted than the scatter corrected image intensity data 98 has the expected shape corresponding to a scatter-free image taken of a test phantom having a uniform thickness.

Alternatively, a different scatter-correction technique may be used. For example, the primary X-rays 42 corresponding to the edge of the slit 44 may be established by subtracting the intensity at the first inflection point 68 from the intensity at the second inflection point 72. If the subject has a uniform thickness, then it can be assumed that the primary X-rays 42 are uniform across the region of the image intensity data 48 that is due both to primary X-rays 42 and scatter 46. Thus, the primary X-rays 42 at the edge represents the primary X-rays 42 across the entire region 50. To determine the scatter 46 in the region 50 of the data 48 due to both primary X-rays 42 and scatter 46, the intensity of the primary X-rays 42 established at the edge is subtracted from the image intensity data 46 across the region 50. Once known, the scatter 46 can then be subtracted from the image intensity data 48 in the region 50.

Referring again to FIG. 5, in the illustrated embodiment, the dual-energy imaging system 20 exposes a patient with X-rays at the second energy level before repositioning to take an image of the next portion of the region of interest, as represented generally by block 100. The techniques described above for acquiring and correcting image intensity data are then repeated for the image intensity data obtained with the X-rays at the second energy level. As will be appreciated by those skilled in the art, various methodologies may be used in practice for generating image data at different energy levels. For example, with the system in each position, image data at both energy levels may be acquired, or the various positions may be traversed to acquire image data at one energy level, and then the same positions may be repeated to acquire image data at the second energy level. Still further, if the system includes a dual energy detector capable of acquiring image data at two different energy levels simultaneously, combined acquisition at the energy levels may be performed.

The X-ray source 26 and the slit collimator 24 are then repositioned to obtain data from a second portion of the patient, as represented generally by block 102. In the illustrated embodiment, the X-ray source 26 and the slit collimator 24 are pivoted, rather than being displaced laterally, to expose the second portion of the patient. The process is repeated as necessary until the series of images of the region of interest have been completed. There may be overlap between the images in the series of images of the patient's region of interest. Alternatively, the system 20 may acquire all of the desired images of the region of interest with X-rays of the first energy level before acquiring any images with the X-rays at the second energy level.

Once the image intensity data 48 for the region of interest of the patient has been acquired, one or more images of the patient are created using the scatter-corrected image intensity data, as represented generally by block 104. The image may be a dual subtracted image of bone and/or soft tissue.

In this embodiment, the scatter-corrected image intensity data, as opposed to non-scatter-corrected image intensity data, is used to establish the BMD, as represented generally by block 106. The BMD may be established without forming the image as represented by block 104. In the illustrated embodiment, the scatter-corrected image intensity data is used to establish equivalent thicknesses of aluminum and Lucite corresponding to the absorption of X-rays within the patient. The equivalent thicknesses are then converted to a BMD score. However, other methods of establishing the BMD from scatter-corrected image intensity data may be used.

Figure 8:
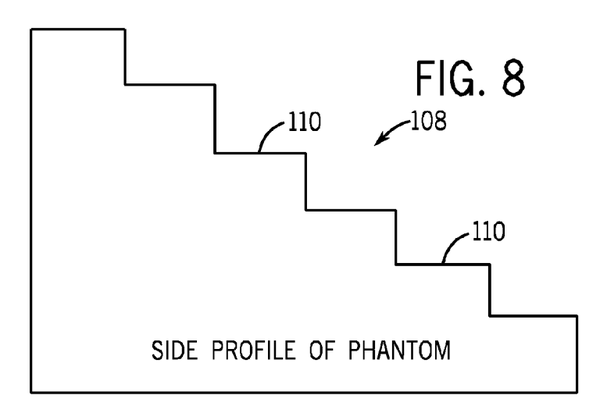
FIG. 8 is an elevation view of a first test phantom, in accordance with an exemplary embodiment of the present technique.

Referring generally to FIG. 8, an elevation view of a test phantom 108 is presented. The phantom is comprised of non-uniform thicknesses of aluminum and Lucite. In this embodiment, the phantom 108 has a series of steps 110 that rise from one side to the next.

Figure 9:
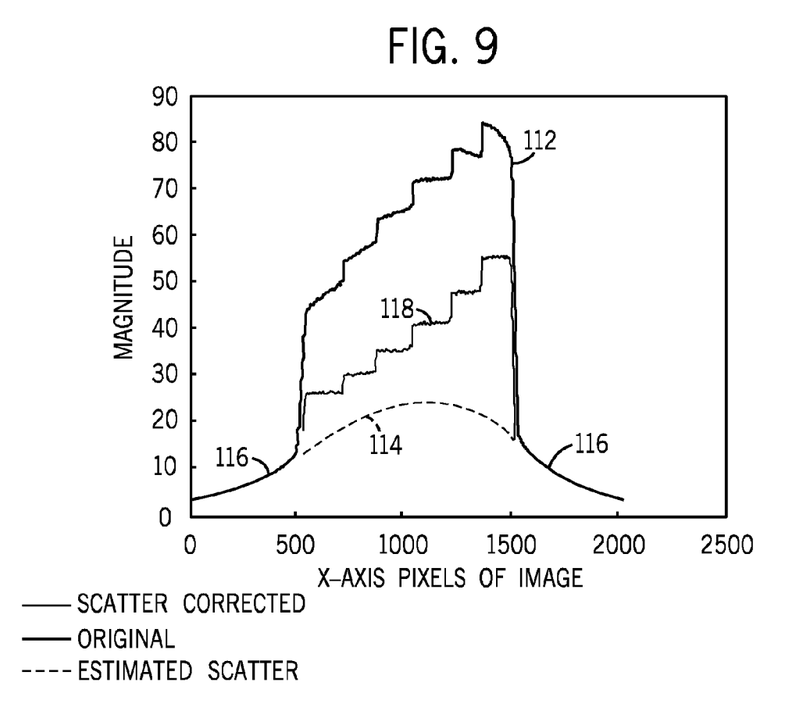
FIG. 9 is an X-axis plot of image intensity, the estimated scatter, and the scatter-corrected image intensity for an image of the first test phantom of FIG. 8, in accordance with an exemplary embodiment of the present technique.

Referring generally to FIG. 9, the results of producing an image of the test phantom 108 using the technique described above is presented. The results include a plot of uncorrected image intensity versus position along the X-axis of the detector 22, referenced generally by reference numeral 112. Note that the plot 112 differs markedly from the shape of the phantom 108. The plot 112 presents a more saw-toothed shape than the flat steps of the phantom 108. A plot of the estimated scatter intensity in the portion of the image intensity data opposite of the slit 44 is also presented, as represented by reference numeral 114. As described above, the uncorrected image intensity data 112 is corrected for scatter by subtracting the image intensity in the scatter-only regions, as represented by reference numerals 116, and the estimated scatter intensity 114 from the uncorrected image intensity data 112. It should be noted that the plot of the scatter-corrected image intensity data, as represented generally by reference numeral 118, has the stepped profile of the phantom 108, rather than the saw-tooth profile of the uncorrected image intensity plot 112.

Figure 10:
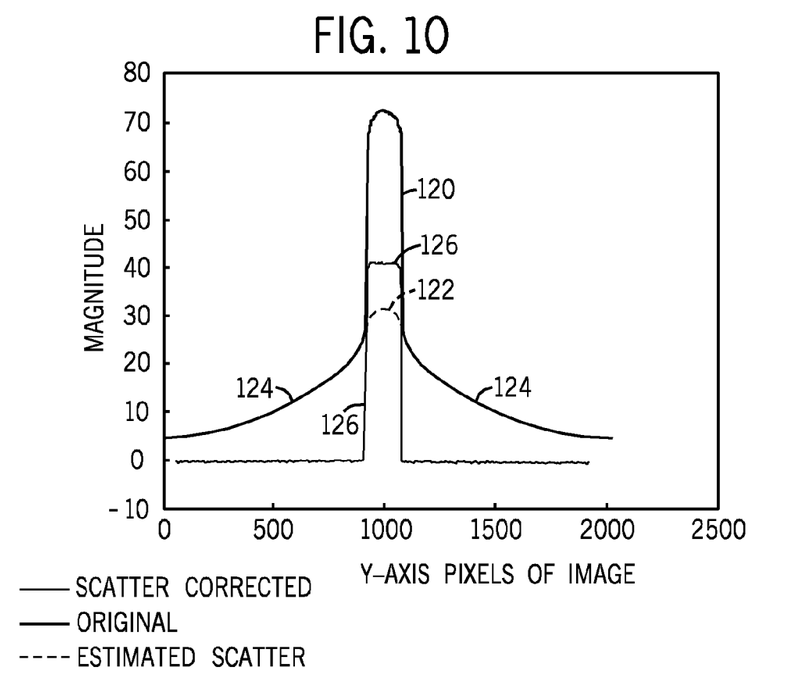
FIG. 10 is a Y-axis plot of image intensity, the estimated scatter, and the scatter-corrected image intensity for an image of the first test phantom of FIG. 8, in accordance with an exemplary embodiment of the present technique.

Referring generally to FIG. 10, a plot of image intensity, the estimated scatter, and the scatter-corrected image intensity along the Y-axis of the detector 22 for an image of the test phantom of FIG. 8 is presented. In the illustrated embodiment, the plot of uncorrected image intensity versus position along the Y-axis of the detector 22, referenced generally by reference numeral 120, has a semicircular top than the expected flat shape of the phantom 108. The plot of the estimated scatter intensity in the portion of the image intensity data opposite of the slit 44 is also presented, as represented by reference numeral 122. The uncorrected image intensity data 120 is corrected for scatter by subtracting the image intensity in the scatter-only regions, as represented by reference numerals 124, and the estimated scatter intensity 122 from the uncorrected image intensity data 120. It should be noted that the plot of the scatter-corrected image intensity data, as represented generally by reference numeral 126, has the expected flat-topped profile of the phantom 108 rather than the semicircular top profile of the uncorrected image intensity plot 120.

Figure 11:
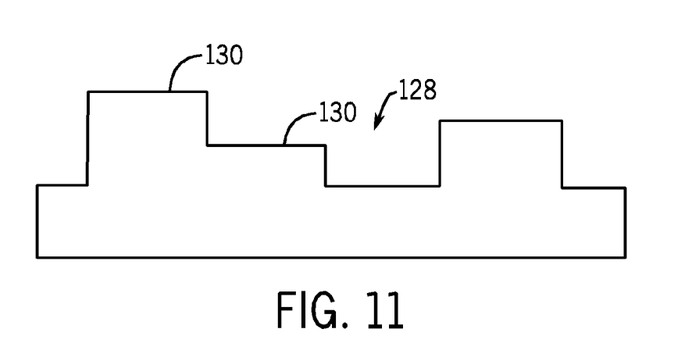
FIG. 11 is an elevation view of a second test phantom, in accordance with an exemplary embodiment of the present technique.

Referring generally to FIG. 11, an elevation view of a second test phantom 128 is presented. The phantom is comprised of non-uniform thicknesses of aluminum and resin. In this embodiment, the phantom 128 has a series of plateaus 130.

Figure 12:
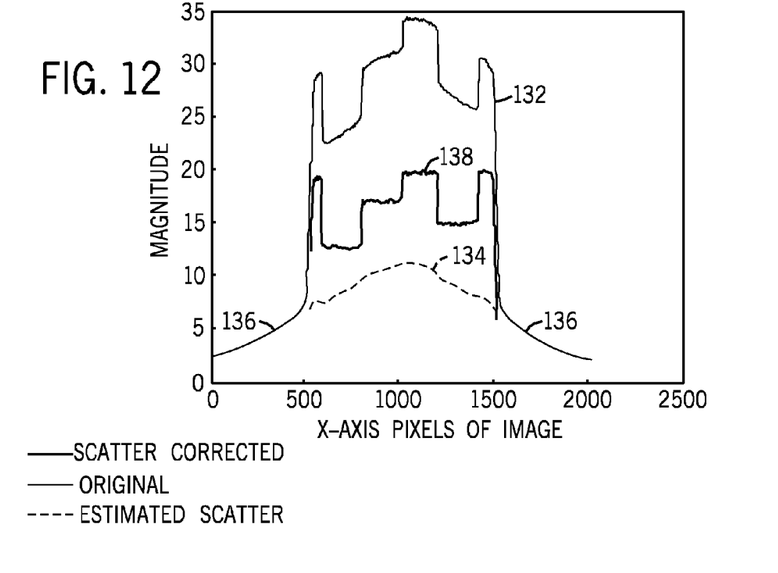
FIG. 12 is an X-axis plot of image intensity, the estimated scatter, and the scatter-corrected image intensity for an image of the second test phantom of FIG. 11, in accordance with an exemplary embodiment of the present technique.

Referring generally to FIG. 12, a plot of image intensity, the estimated scatter, and the scatter-corrected image intensity along the X-axis of the detector 22 for an image of the test phantom of FIG. 11 is presented. In the illustrated embodiment, the plot of uncorrected image intensity versus position along the X-axis of the detector 22, referenced generally by reference numeral 132, has more curvature than the flat plateaus 130 of the phantom 128. The estimated intensity of the scatter in the region of the image intensity data opposite the slit 44 is established using the technique described above. A plot of the estimated scatter intensity in the portion of the image intensity data opposite of the slit 44 is also presented, as represented by reference numeral 134. As described above, the uncorrected image intensity data 132 is corrected for scatter by subtracting the image intensity in the scatter-only regions, as represented by reference numerals 136, and the estimated scatter intensity 134 from the uncorrected image intensity data 132. Note that the plot of the scatter-corrected image intensity data, as represented generally by reference numeral 138, has the flat plateaus of the phantom 128 rather than the curvature of the uncorrected image intensity plot 132.

Figure 13:
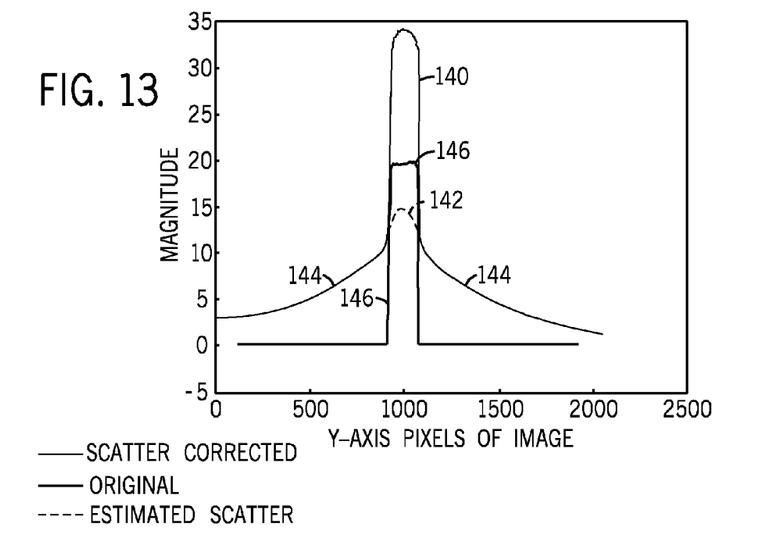
FIG. 13 is a Y-axis plot of image intensity, the estimated scatter, and the scatter-corrected image intensity for an image of the second phantom of FIG. 11, in accordance with an exemplary embodiment of the present technique.

Referring generally to FIG. 13, a plot of image intensity, the estimated scatter, and the scatter-corrected image intensity along the Y-axis of the detector 22 for an image of the test phantom of FIG. 8 is presented. In the illustrated embodiment, the plot of uncorrected image intensity versus position along the Y-axis of the detector 22, referenced generally by reference numeral 140, has a semicircular top than the expected flat shape of the phantom 128. The plot of the estimated scatter intensity in the portion of the image intensity data opposite of the slit 44 is also presented, as represented by reference numeral 142. The uncorrected image intensity data 140 is corrected for scatter by subtracting the image intensity in the scatter-only regions, as represented by reference numerals 144, and the estimated scatter intensity 142 from the uncorrected image intensity data 140. Note that the plot of the scatter-corrected image intensity data, as represented generally by reference numeral 146, has the expected flat-topped profile of the phantom 128 rather than the semicircular top profile of the uncorrected image intensity plot 140.

The technical effect of the technique is to correct image intensity data for scatter. While only certain features of the invention have been illustrated and described herein, many modifications and changes will occur to those skilled in the art. It is, therefore, to be understood that the appended claims are intended to cover all such modifications and changes as fall within the true spirit of the invention.

The invention claimed is:

1. A computer-implemented method for processing image data, comprising:
    accessing image intensity data obtained by a digital imaging detector, wherein the image intensity data comprises a first region that is produced by primary X-rays and scatter and at least one second region that is produced by scatter only;
    identifying within the image intensity data the first region that is produced by primary X-rays and scatter and the at least one second region that is produced by scatter only based upon a derivative of the image intensity data;
    establishing scatter intensity in the at least one second region of the image intensity data that is produced by scatter only;
    estimating scatter intensity in the first region of the image intensity data based on the scatter intensity in the at least one second region of the image intensity data; and
    correcting the first region of the image intensity data for scatter based on the estimated scatter intensity in the first region to establish scatter-corrected image intensity data.

2. The computer-implemented method for processing image data as recited in claim 1, comprising:
    establishing bone mineral density within a portion of a patient based on scatter-corrected image intensity data.

3. The computer-implemented method for processing image data as recited in claim 1, wherein correcting the first region of the image intensity data for scatter comprises subtracting the estimated scatter intensity from the image intensity data.

4. The computer-implemented method for processing image data as recited in claim 3, comprising:
    correcting the at least one second region of the image intensity data for scatter by subtracting the at least one second region from the image intensity data.

5. The computer-implemented method for processing image data as recited in claim 1, comprising:
    identifying at least one abrupt change in the derivative of the image intensity data, wherein the at least one second region of the image intensity data is defined by the at least one abrupt change in the derivative of the image intensity data.

6. The computer-implemented method for processing image data as recited in claim 1, wherein establishing an estimated scatter intensity in the first region of the image intensity data comprises multiplying a scatter intensity by a correction factor to estimate scatter intensity at a point of the first region of the image intensity data.

7. The computer-implemented method for processing image data as recited in claim 6, comprising:
    identifying at least one abrupt change in the derivative of the image intensity data, wherein the scatter intensity multiplied by a correction factor is based on at least one scatter intensity corresponding to the at least one abrupt change in the derivative of the image intensity data.

8. The computer-implemented method for processing image data as recited in claim 6, wherein establishing an estimated scatter intensity comprises interpolating scatter intensity within the first region of the image intensity data based on the estimated scatter intensity at a point of the first region of the image intensity data.

9. The computer-implemented method for processing image data as recited in claim 6, wherein the correction factor is based on a patient's characteristic.

10. The computer-implemented method for processing image data as recited in claim 9, wherein the patient's characteristic is entered manually.

11. The computer-implemented method for processing image data as recited in claim 9, wherein the patient's characteristic is retrieved automatically from an electronic record.

12. The computer-implemented method for processing image data as recited in claim 9, wherein the patient's characteristic is a relative size of the patient.

13. The computer-implemented method for processing image data as recited in claim 1, wherein accessing image intensity data obtained by a digital imaging detector comprises accessing image intensity data obtained by a flat-panel digital X-ray detector from X-rays produced by an X-ray source through a slit collimator.

14. The computer-implemented method for processing image data as recited in claim 1, wherein accessing image intensity data obtained by a digital imaging detector comprises accessing intensity data obtained by a dual-energy digital X-ray imaging system.

15. A system for computer for processing image data, comprising means for accessing image intensity data obtained by a digital imaging detector, wherein
    the image intensity data comprises a first region that is produced by primary X-rays and scatter and at least one second region that is produced by scatter only;
    means for identifying within the image intensity data the first region that is produced by primary X-rays and scatter and the at least one second region that is produced by scatter only;

means for establishing scatter intensity in the at least one second region that is produced by scatter only based upon a derivative of the image intensity data;

means for estimating scatter intensity in the first region of the image intensity data based on the scatter intensity in the at least one second region of the image intensity data; and means for correcting the first region of the image intensity data for scatter based on the estimated scatter intensity in the first region to establish scatter-corrected image intensity data.

16. A non-transitory computer-readable storage medium storing computer-executable instructions for processing medical image data, comprising:

code operable to access image intensity data obtained by a digital imaging detector, wherein the image intensity data comprises a first region that is produced by primary X-rays and scatter and at least one second region that is produced by scatter only;

code operable to identify within the image intensity data the first region that is produced by primary X-rays and scatter and the at least one second region that is produced by scatter only, based upon a derivative of the image intensity data;

code operable to establish scatter intensity in the at least one second region that is produced by scatter only;

code operable to estimate scatter intensity in the first region of the image intensity data based on the scatter intensity in the at least one second region of the image intensity data; and code operable to correct the first region of the image intensity data for scatter based on the estimated scatter intensity in the first region to establish scatter-corrected image intensity data.

17. A computer-implemented method for processing image intensity data, comprising:

identifying a first region within the image intensity data that is produced by scatter only based on rates of change of image intensity within the image intensity data;

establishing an estimated scatter intensity in a second region of the image intensity data that is produced from primary X-rays and scatter based on scatter intensity at a point in the first region of the image intensity data that is proximal to the second region of the image intensity data; and correcting the second region of the image intensity data for scatter based on the estimated scatter intensity in the second region;

wherein identifying a first region within the image intensity data that is produced by scatter only based on rates of change of image intensity within the image intensity data comprises establishing a derivative of the image intensity data and identifying the first region based on abrupt changes in the of the image intensity data.

18. The computer-implemented method for processing image data as recited in claim 17, comprising:

establishing bone mineral density within a portion of a patient based on scatter-corrected image intensity data.

19. The computer-implemented method for processing image data as recited in claim 17, comprising: accessing image intensity data obtained by a flat-panel digital imaging detector from X-rays produced by an X-ray source via a slit collimator.

20. The computer-implemented method for processing image data as recited in claim 19, wherein accessing image intensity data obtained by a flat-panel digital imaging detector from X-rays produced by an X-ray source via a slit collimator comprises accessing intensity data produced by a dual-energy digital X-ray imaging system.

21. The computer-implemented method for processing image data as recited in claim 17, wherein the point in the first region of the image intensity data that is proximal to the second region of the image intensity data corresponds to an abrupt change in the derivative of the image intensity data.

22. The computer-implemented method for processing image data as recited in claim 17, wherein establishing the estimated scatter intensity comprises multiplying a value for scatter corresponding to scatter intensity at a point in the first region of the image intensity data that is proximal to the second region of the image intensity data by a correction factor to establish an estimate for scatter intensity at least one point of the second region of the image intensity data.

23. The computer-implemented method for processing image data as recited in claim 22, wherein establishing an estimated scatter intensity comprises interpolating scatter intensity between the estimate for scatter intensity at least one point of the second region of the image intensity data and the point in the first region of the image intensity data that is proximal to the second region of the image intensity data of the image intensity data.

24. The computer-implemented method for processing image data as recited in claim 22, wherein the value for scatter comprises an average of a first scatter intensity corresponding to a first abrupt change in a derivative of the image intensity data and a second scatter intensity corresponding to a second abrupt change in a derivative of the image intensity data.

* * * * *